United States Patent [19]
Roos et al.

[11] Patent Number: 5,888,215
[45] Date of Patent: Mar. 30, 1999

[54] LOWER EXTREMITY PROSTHESIS

[76] Inventors: Birger Roos, Ursviksvägen 5, S-172 36 Sundbyberg, Sweden; Urban Lindgren, Ottevägen 51, S-102 42 Stockholm, Sweden; Hannu Määttänen, Schylandersvägen 1, S-129 43 Hägersten, Sweden

[21] Appl. No.: 793,785
[22] PCT Filed: Aug. 15, 1995
[86] PCT No.: PCT/SE95/00924
   § 371 Date: Jun. 18, 1997
   § 102(e) Date: Jun. 18, 1997
[87] PCT Pub. No.: WO96/05785
   PCT Pub. Date: Feb. 29, 1996

[30] Foreign Application Priority Data

Aug. 25, 1994 [SE] Sweden .................................. 9402844

[51] Int. Cl.⁶ .................................................. A61F 2/80
[52] U.S. Cl. ............................................. 623/33; 623/16
[58] Field of Search ................................ 623/32, 33, 27, 623/28, 34–38, 57, 21, 47, 59, 53, 16, 49

[56] References Cited

U.S. PATENT DOCUMENTS

| | | |
|---|---|---|
| 3,947,897 | 4/1976 | Owens . |
| 4,158,895 | 6/1979 | Reswick et al. ........................ 623/57 |
| 4,547,912 | 10/1985 | Sherva-Parker ......................... 623/57 |
| 5,041,137 | 8/1991 | Nemoshkalov . |
| 5,180,383 | 1/1993 | Haydon . |
| 5,507,835 | 4/1996 | Jore ....................................... 623/33 |

FOREIGN PATENT DOCUMENTS 504103 9/1992 European Pat. Off. .

Primary Examiner—Mary Beth Jones
Assistant Examiner—Bruce E. Snow
Attorney, Agent, or Firm—Sughrue, Mion, Zinn, Macpeak & Seas PLLC

[57] ABSTRACT

A lower extremity prosthesis solves the problem of relieving the end of the leg stump (S) from a portion of the vertical forces acting on it by pressure from the socket (1) surrounding and supporting the stump, by providing a mechanism capable of transferring forces to the tibia (T). The mechanism includes a first member (13) connected to the tibia and second members (5, 8) detachably connected to the first member and carried by the socket.

11 Claims, 4 Drawing Sheets

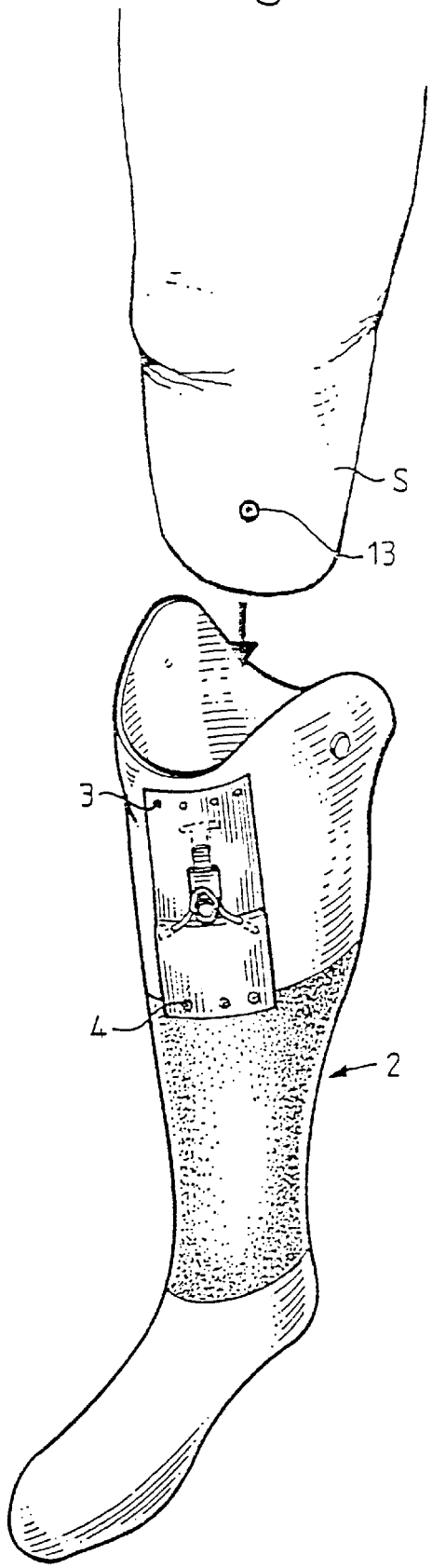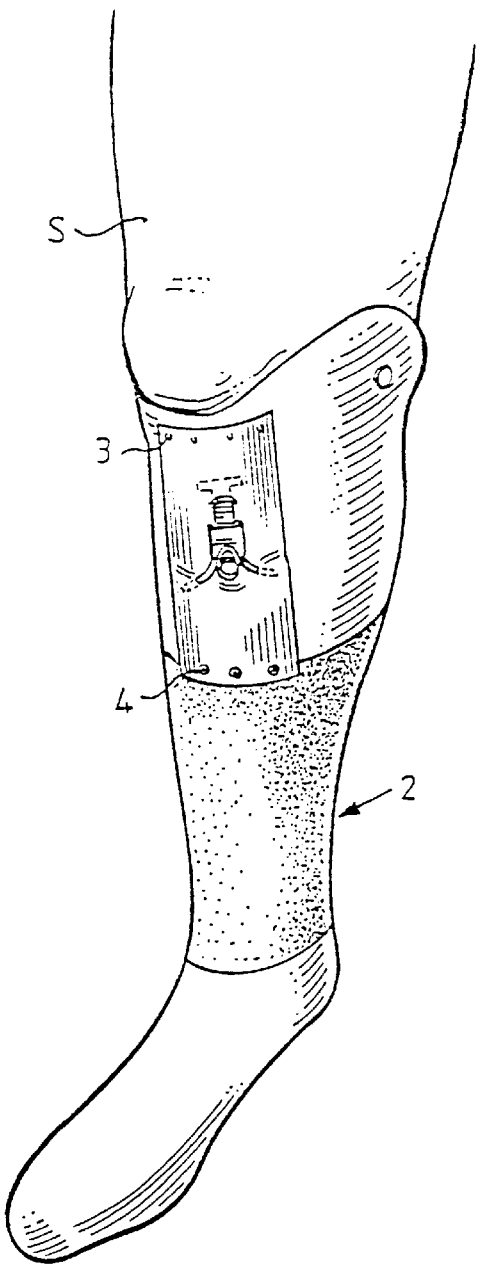

LOWER EXTREMITY PROSTHESIS

BACKGROUND OF THE INVENTION

The present invention relates to a lower extremity prosthetic fitting which is improved in respect of the transfer of loading forces between the fitting and the skeleton parts inside the shortened leg, the stump. Irrespective of whether the reason for the shortening was morbid changes of the lower portion of the leg which made it necessary to remove that portion by amputation, for instance due to diabetes, or the result of an accident, e.g. a traffic accident, the residual part of the lower extremity will assume the shape of a stump in which the skeleton parts are both laterally and at their lower ends surrounded by soft tissues. When, following healing after the shortening, a lower extremity prosthesis is to be fitted, this fitting is provided with a socket open at its top end and tapering in the downward direction. It is intended to surround the stump and at its lower, closed end connected to an artificial foot. The function of the socket is to maintain the fitting connected to the stump. In order for the fitting to fulfill that function the internal shape of the socket must in a special way match the shape of the stump so that the loading forces acting on the foot can be transferred to the stump and from there further on to the knee-joint, the thigh-bone and the hip-joint.

The first step in that force transfer, from the socket to the knee-joint, takes place via the residual part of the tibia. However, this transfer will be indirect in the sense that as mentioned above, this skeleton member is surrounded by soft tissues also at the bottom of the stump. These soft portions are deformed, especially during the transfer of the substantially vertically oriented forces which occur when the patient is standing, when he walks and, generally, when the distance between the artificial foot and the thigh is varying. In such situations there occurs a relative movement between the stump and the socket. This movement, in the vertical direction often referred to as "pumping" and in the transversal direction as "staggering", is undesired for two reasons. One reason is that the play results in instability and the second reason that it may, in combination with the pressure against the soft portions, develop infections and wounds, in the most serious cases to such an extent that the prosthesis must not be used during a longer or shorter period of time.

There does accordingly exist a need for a possibility, to the extent desired, to replace this indirect transfer of forces to the tibia, that is via the remaining soft portions of the leg below the knee-joint, by a rigid, mechanical transfer direct to the tibia, which would result in a corresponding elimination of the possibility of pumping and staggering including their detrimental consequences.

It is prior art in thigh-leg prostheses to attain such a stress-relief by a rigid force transfer from the prosthesis directly to the skeleton member in the thigh. In such prior art designs the connection to the thigh-bone has been created by means of a pin extending vertically upwards from the bottom of the socket and entering an axial bore from the bottom end of the thigh-bone. It is, however, for several reasons very difficult to use such a force transfer arrangement in low extremity prosthetic fittings. Those reasons are due to the anatomical differences, in terms of different thicknesses and different shapes, which exist between a thigh-bone and a tibia. In both those cases the bone tissue proper surrounds an axial extending space containing bone-marrow. While the thigh-bone, femur, exhibits a great transversal dimension—it is the thickest bone of the skeleton—and is almost circular in cross-section, the tibia is considerably more narrow and substantially triangular in cross-section. Further, its wall thickness is considerably less. Also in a grown up person it normally amounts to just 3–5 mms and, quite naturally, in children the tibia wall surrounding the central bone-marrow space is still thinner. In this context it must also be noted that the force-absorbing ability of a pin inserted axially in the bone-marrow space is limited as far as lateral forces are concerned. While it is true that such lateral forces are of a negligible magnitude when the amputee is standing still in an upright position, they increase to considerable magnitudes when he is walking in which situation also dynamic force components are added. Should the amputee for instance kick or slip, these forces become very high. For those reasons orthopaedists and prosthesis-technicians have had to establish that so far they have not succeeded to solve the pumping problem, its related inconveniences and the risks for the patients, by using in lower extremity prosthetic fittings the same type of mechanisms for transferring forces between the fitting and the skeleton members of the extremity as can be used in thigh-bone prostheses.

SUMMARY OF THE INVENTION

However, this problem has now been solved thanks to the present invention which makes possible a direct transfer of a greater or smaller share of the forces from the prosthesis to the tibia in another way than by the use of an axial pin, namely so that some of the loading forces are transferred to the tibia in a lateral direction. The remaining part of the forces is in the normal manner transferred via the socket. Actually, the share of the forces transferred via a mechanism according to the present invention needs to amount to a smaller portion of the total force only in order to result in a reduction of the stump problems. The realization that this is a possible solution of those problems constitutes the new and most important part of the inventive concept. It should however be underlined that this new principle does not only involve a displacement from one position to another of the point of application of the loading forces. Just the other way round the situation is that, when the just-mentioned inventive concept is to be applied in practice, there will arise several detail issues, both of a medical and of a mechanical nature. However, the invention includes replies also to such questions, to which reference will be made below. A great advantage of the invention is that the surgical intervention is small.

Before proceeding to the special portion of the description I will, however, first further illuminate the interaction between the forces in a lower extremity prosthesis.

When an amputee equipped with a prosthesis is standing or sitting still, naturally only static pressure forces are in play and—when the leg is in a vertical position—these forces become vertically oriented. When the foot is suspended freely, there will exist a pulling force between the fitting and the stump which force, when the foot rests against the floor, will change to a pushing stress. In the latter case the weight of the leg or that of all of the body, respectively, will generate a reaction force directed upwards which tends to compress the soft tissues between the bottom of the socket and the stump. In the first-mentioned case, when the foot is lifted above the floor surface, the pulling force directed downwards corresponds to the sum of the weight of the fitting proper and the shoe of the amputee. As is understood, in that position the just mentioned soft tissues are deloaded, which results in an increased degree of pumping due to the play between the stump and the socket then arising.

When the person is walking there are also generated dynamic forces which are added to the static forces by an amount typically around 20% and sometimes up to approximately 50%. One of those additional forces is the longitudinal force (as seen in the longitudinal-axis direction of the leg) which is generated each time the artificial foot comes into contact with the ground surface and the other foot is more or less deloaded. Another such dynamic force is the torsional force generated when the artificial foot is exposed to a torque, generally oriented in a horizontal plane and counteracted by the friction against the underlying surface. Thirdly, when he is walking, there are generated dynamic forces tending to incline the fitting relatively the tibia. Those forces can, from a stress-loading point of view, be divided into two components, one of them oriented in the walking direction and the other perpendicularly thereto. If the longitudinal force is assumed to be about 50% greater than the weight of the body, it will amount to about 1000N. The two tip forces may generate torques of the order of magnitude of 30 Nm. It has empirically been found that the resultant of all those forces may grow to such a value that the soft tissue layer in the bottom portion of the stump yields pains or inconveniences, sometimes injuries.

A force transmission according to the present invention has the decisive advantage that the soft portions of the leg stump are deloaded thanks to the fact that they are no longer exposed to all of the vertical pressure component of the transfer forces which may instead—to a greater or lesser degree—be transferred directly to the skeleton from the lateral wall of the socket. As mentioned above, this has not previously been considered possible in this type of prostheses. This invention has made it possible by the use of a force transfer member extending transversally, i.e. "diametrically", through the tibia. Also such transversal forces which tend to create staggering of the stump in the socket may to a greater or less extent be transmitted via such means.

BRIEF DESCRIPTION OF THE DRAWINGS

FIGS. 3 and 4 are perspective views showing the fitting and the leg stump in a ready-for-entry position and in a mounted position, respectively.

DETAILED DESCRIPTION OF THE PREFERRED EMBODIMENTS

Figure 1:
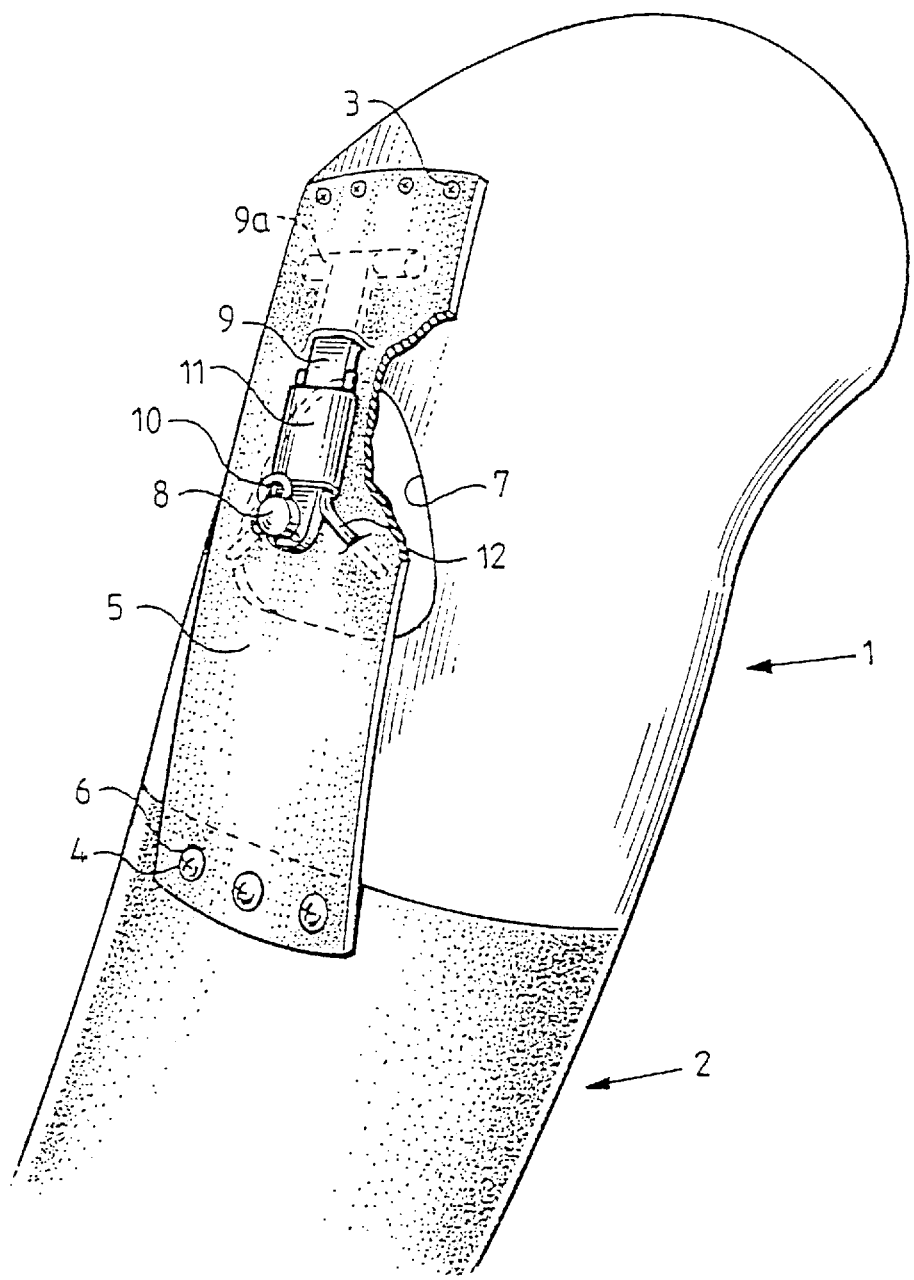
FIG. 1 is a perspective view showing the externally visible part of a fitting according to one embodiment of the invention.

The parts of the fitting visible in FIG. 1 are a socket 1 which in a manner known per se is shaped to match the leg stump and which suitably consists of a plastic material. For cosmetic reasons a sock 2 covers part of the socket. A resilient plate 5, is by means of upper fixation members 3 and lower fixation members 4, secured substantially above the sock. The fixation means may be constituted by for instance screws which engage socket 1. The resilient plate consists of a high-quality elastic material such as urethan rubber. In the front wall of the socket there is an opening 7 which is covered by plate 5. A ball pin 8 extends through the plate and through the opening. Its detailed configuration will be described below with reference to FIG. 2. In FIG. 1 there is visible only the head of the pin which extends through a control arm 9. The head is rotatable so that a bayonet catch of the ball pin can be locked and unlocked. Numeral 10 designates a cotter pin. The control arm supports two wire-shaped arms 12. These can be vertically turned and displaced in a sleeve 11, secured to the control arm. Their purpose is to distribute the force from the ball pin and the control arm to all of the width of the resilient plate. The possibility to displace the two arms longitudinally is relied upon when the amputee desires, in a sitting position, to pull out the stump somewhat from the socket. The ball pin will then move in the elongate hole in plate 5. The control arm has a transversal yoke 9a, which by being clamped between the resilient plate and the sleeve limits the possibility of the control arm to turn around its vertical longitudinal axis.

Figure 2:
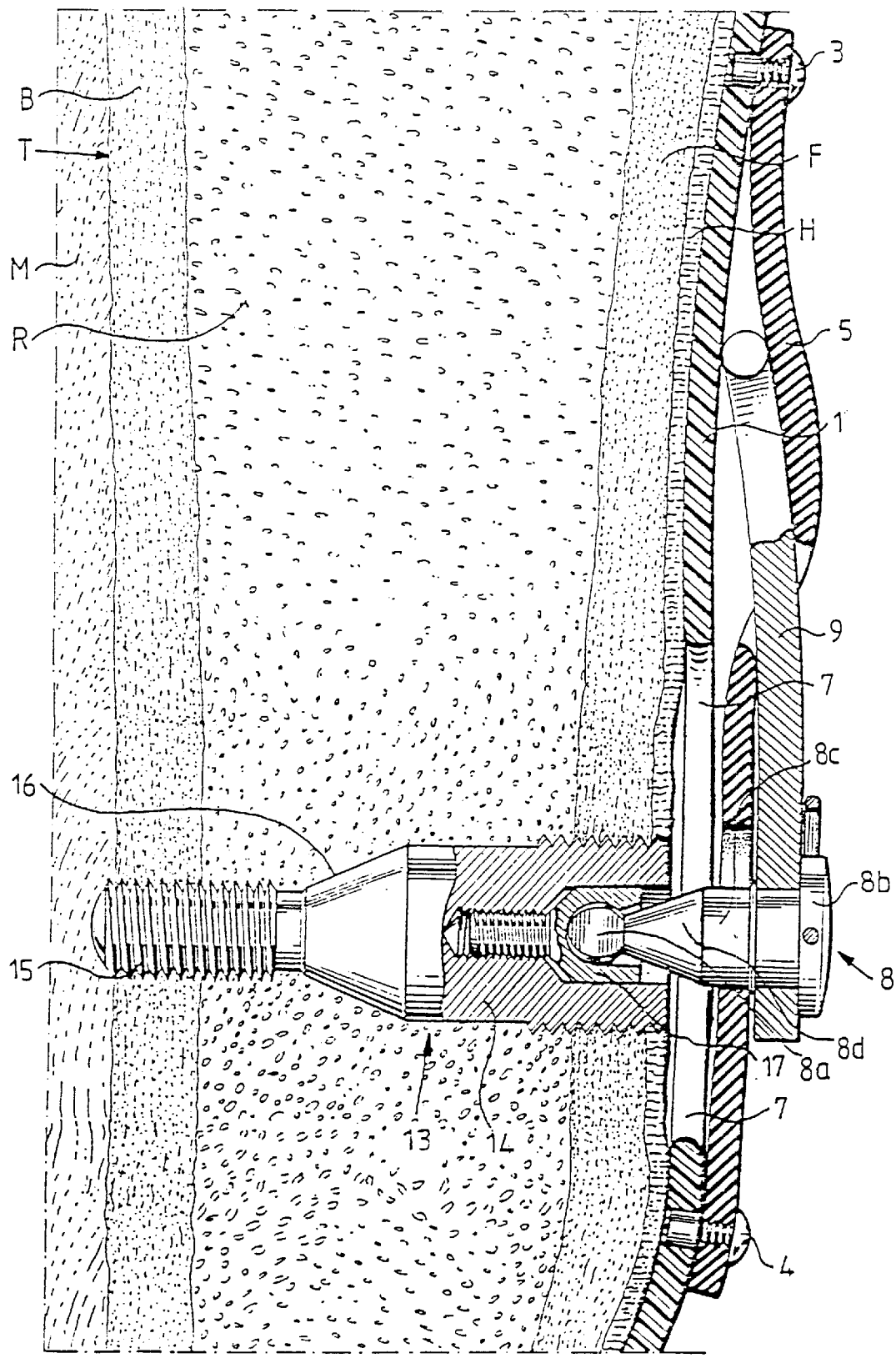
FIG. 2 does, on a greater scale, show a vertical section through the fitting and through a portion of the tibia to which the fitting is connected.
Figure 5:
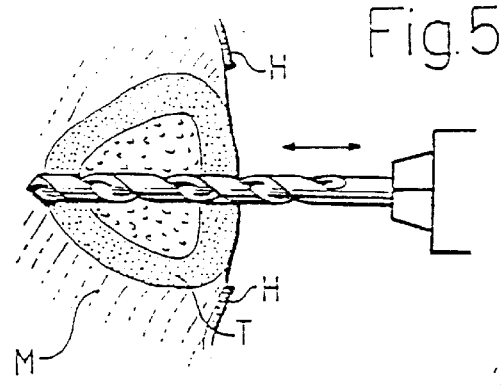
FIGS. 5–10 are horizontal cross-sectional views illustrating the various working steps of a method for mounting those parts of the fitting which are to be anchored in the tibia.

The cross-section in FIG. 2 illustrates the parts of the mechanism not visible from the outside. As mentioned above, FIG. 2 is a vertical section on an enlarged scale through a tibia with a force transfer mechanism and an implanted skeleton screw according to the invention. It is important to note that the resilient plate 5 is located at the front side of the fitting but angularly displaced inwards approximately 45°. In FIG. 2 reference letter T refers to the tibia. Letters F and B refer to the front and back walls of the tibia which along the major portion of its circumference is surrounded by muscular tissue M and substantially triangular in cross-section. However, on the front side there is practically no muscular tissue, just a thin fat coating under the skin H. The invention takes advantage of that fact which will be explained below. In the area of the window opening 7, suitably in its center, the tibia is traversed by a skeleton screw 13 having a thicker cylindrical section 14 passing through the front wall F of the tibia, a thinner section 15, traversing the back wall B of the tibia, and an intermediate conical section 16. As illustrated in the drawing, the two cylindrical sections of the skeleton screw have threads in engagement with the adjacent portions of the tibia in which holes have been drilled as will be explained below.

In the thicker section 14 of skeleton screw 13 there is a cavity housing a member which constitutes a ball retainer with a bayonet lock. It is referenced 17 and does likewise comprise an inner, thinner section and an outer, thicker section. The latter has external threads engaging corresponding internal threads in the smaller section of the cavity. The thicker section of the ball retainer has an outwardly open chamber receiving the spherical ball 8a and it is shaped so as to form a seating for the ball. The contour line of the opening corresponds the shape of the ball which has two flat-ground segments so that a bayonet lock is formed. The ball pin does, in addition to the head 8b, also comprise a cylindrical portion 8c, likewise located outside the window 7 and via an inwardly tapering section 8d integrally connected with the ball.

The mode of operation of the mechanism for transferring forces between the skeleton and the socket is as follows. The lateral position of ball 8a is substantially central in the bone wall. Accordingly, forces in the longitudinal direction of the leg and in the one transversal direction are relatively smoothly transferred to the bone tissue from the thicker section of the skeleton screw. Forces in the second transversal direction, i.e. in the axial direction of the skeleton screw, are also transferred in a favourable way via the threads at both ends of the screw. When the tibia, in response to various movements in the soft tissues of the stump, moves the ball pin, resilient plate 5 will counteract those movements. Thanks to the fact that the plate can be biased and given different dimensions, the magnitude of the transmitted forces can be selected to match the conditions in each individual. The combined functional contributions from the skeleton screw, the ball pin, the control arm and the resilient plate are characteristic for the invention. The bias has been attained by means of fixation screws 3 and 4. Naturally, it is necessary that the patient can himself remove the fitting, for example when going to bed, which he does by pulling the external parts of the mechanism outwards so that ball 8*a* leaves its seating.

Figure 6:
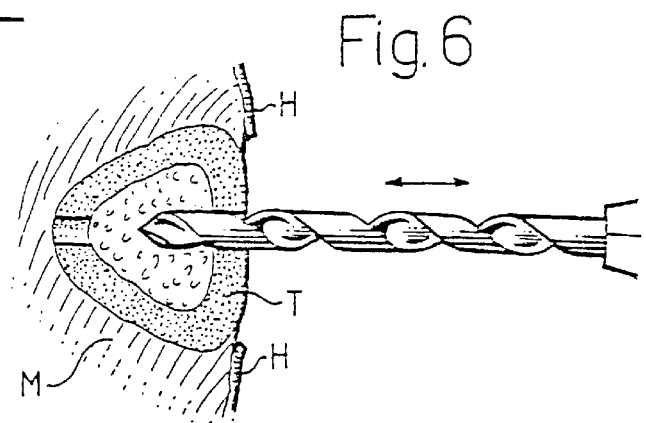
Figure 7:
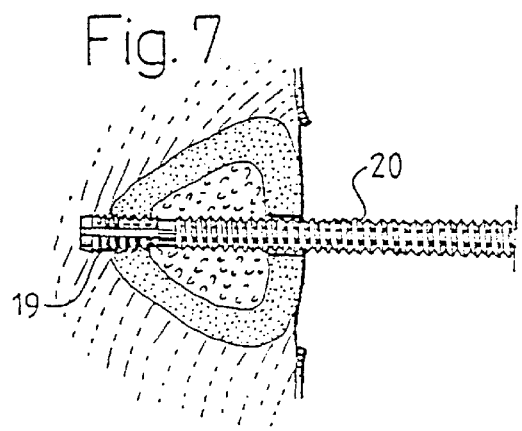
Figure 8:
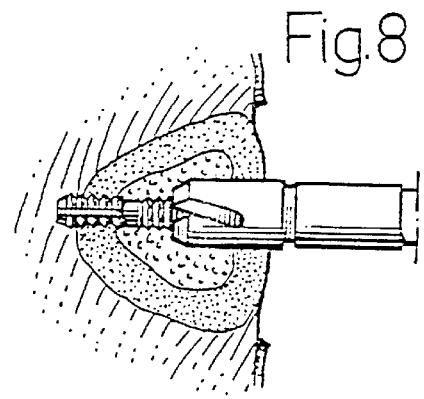
Figure 9:
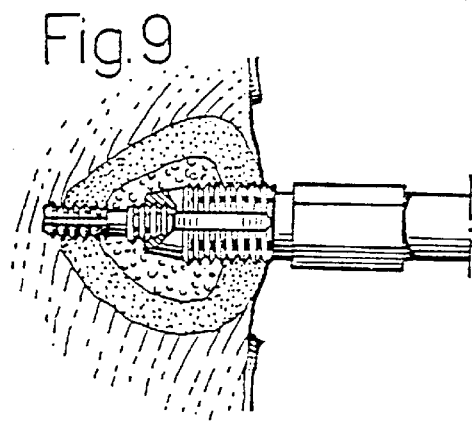
Figure 10:
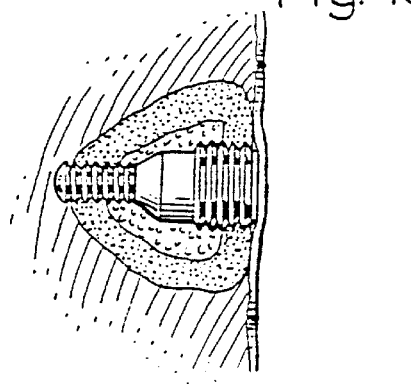

FIGS. 5–10 exemplify how to mount those parts of the mechanism which are permanently secured to the tibia, i.e. osseo-integrated. The drawing shows horizontal cross-sections through the tibia T. Adjacent muscular tissues M and the skin H have also been shown. The first step of the operation is to cut out a substantially semi-circular skin flap having a height of about 40 mms and a width of about 20 mms, whereupon the flap is folded upwards. The next step is to drill a hole about 25 mms above the bottom end of the bone. The diameter of the drill should not exceed the core diameter of the thread on the narrow end section 15 of the skeleton screw. As shown in the drawing, the drilling is performed to such a depth that the rear as well as the front wall of the tibia are penetrated. The drill is then replaced by a thicker one, shown in FIG. 6, the diameter of which is somewhat less than the external diameter of the thread tap 19 and its extension 20, shown in FIG. 7. The drill in FIG. 6 does only pass through the front hole. The next step is that thread tap 19 and its extension 20, the diameter of which corresponds the diameter of the thicker drill in FIG. 6, are inserted through the hole in the front wall of the tibia and further in so that tap 19 creates internal threads in the rear tibia wall and slightly less deep threads in the front wall. This has been shown in FIG. 7. Retaining the thread tap in its position the next step, shown in FIG. 8, is to expand the front hole so that its diameter equals the core diameter of the thicker section 14 of the skeleton screw. The drill is hollow and its cavity receives extension 20. Thanks to the fact that tap 19 and said extension remain in position the thicker drill will be accurately centred relatively the tap. Stated in other words this obviously means that the two holes in the front and the rear wall of the tibia become coaxial. The last-mentioned drill is removed from the extension and replaced by an, equally tubular, thread tap having internal threads in engagement with the threads on the tap extension 20, and external threads, creating the internal threads in the front wall of the tibia which are to engage the thicker section 14 of the skeleton screw. Finally, the thread taps are removed whereupon screw 13 can be mounted as shown in FIG. 10. Finally, the skin flap is folded back into position and secured by sewing. The skeleton screw is now implanted in the tibia and the corresponding healing process requires a couple of months. During that time period the bone tissue is integrated with the surface layer of the skeleton screw. The patient may during that time be temporarily equipped with a conventional prosthesis having a orifice around the screw position so that he can walk without disturbing the surgery spot.

The selection of material in the skeleton screw is critical. It is per se previously known that pure titanium is superior, not only to other metals like stainless steel, but also to titanium alloys. In practical applications "pure" means a purity of 99,75%. From other types of prostheses, especially within dental surgery, it is since three decades known that components of pure titanium quickly oxidize on their surface so that there is formed a layer of titaniumperoxide. This layer yields a barrier function against chronical tissue inflammation and becomes incorporated in the cells of the surrounding tissues thereby counteracting repelling phenomena. This phase of the healing period, during which the biocompatible material titanium is integrated with the bone tissue to a stable compound and the skin flap will become secured on the tibia, is typically 6–8 weeks. Following the end of this period a hole is punched through the skin flap. Fat tissue under the skin adjacent the screw is removed so that the skin gets a possibility to attach itself to the underlying bone tissue. Next the skin is left to heal, which again requires a few days, whereupon the ball screw 17 is screwed into the skeleton screw. This concludes the mounting of all mechanism members to be permanently implanted. What now remains is to mount the detachable external members, i.e. the ball pin 8 and the other means already described above in connection to FIGS. 1 and 2.

The importance of selecting pure titanium for the implanted members has been emphasized above. It should also be underlined that the dimensioning of the different members is critical irrespective of the fact that variations between individual patients must be allowed to match the equipment to the weight and the size of the body. Nevertheless the following dimensioning data may serve as a guidance. The diameter of the threaded hole in the front wall of the tibia should be about 12 mms and in the rear tibia wall about 6 mms. A suitable pitch is about 1 mm. As has been mentioned above, it is also to be noted that the force transfer to the tibia taking place in a device according to the invention does not handle the total force system. Instead, the situation is that the implanted mechanism and the socket cooperate. For that reason it is important that the socket is, in an anatomical sense, optimally matched to the shape of the stump since some of the forces are still transferred from the socket to the stump. There does consequently occur a direct force transfer from the stump to the socket, to the mechanism and to the tibia with a partial "short-circuiting" of the soft tissues in the stump. On the other hand, the force transmission between the socket and the stump passes those soft tissue regions.

The cooperation from a force-transfer point of view between the mechanism and the socket is especially important after the healing period. By exchanging parts of the mechanism, or by making it variable without the need of such an exchange, one can during that period of time successively increase the share of the total forces which are transmitted via the mechanism up to the point of time when it is absolutely certain that the skeleton screw is implanted in the tibia in a complete and stable way. When the skeleton screw is exposed to loads a successive growth of bone material will take place resulting in an increased strength.

An arrangement according to the invention may be modified in several respects as far as the detailed structure of the mechanism is concerned. In some cases it may be advantageous to have two screws sharing the load between them. The only essential requirement is that the mechanism is designed so that the soft portions of the stump can be partially relieved of the static and dynamic forces. In this context it is a fundamental feature, instead of a, theoretically imaginable, connection comprising an axially upwardly directed pin inserted in the tibia, to use a member extending laterally into the tibia and anchored into mutually opposite parts of its bone wall. However, the switching from axial to lateral connection also entails other advantages than those resulting from the corresponding displacement of the position at which the forces are introduced into the skeleton. These advantages are related to the fact that the front of the tibia is not covered by muscular tissues but, essentially, only by a thin skin layer. This eliminates the difficult sealing problems which in upper extremity prostheses comprising axial pins often generate wounds and risk of infection.

We claim:

1. A lower extremity prosthesis, comprising a socket (1) having an upper portion adapted to surround a residual leg stump (S), located below the knee, and a lower portion carrying an artificial foot, wherein, at a front of the socket, said socket is provided with a mechanism adapted to transfer forces from the prosthesis directly to a tibia (T) of the stump, said mechanism comprising first means (13), adapted to extend transversely through the tibia from a front side thereof, and second means (5, 8) detachably connected to said first means and mounted on said socket.

2. A prosthesis as claimed in claim 1, wherein said first means (13), for implantation in the tibia, is adapted to be permanently anchored in recesses located opposite each other in front and back wall portions (F, B,) of the tibia.

3. A prosthesis as claimed in claim 2, wherein said first means (13) comprises sections (14, 15) provided with external threads for engagement with said recesses in the tibia.

4. A prosthesis as claimed in claim 2, wherein said first means (13) has a thicker, cylindrical section (14) for engagement with the recess in the front wall portion of the tibia, and a narrower cylindrical section (15) for engagement with the recess in the back wall portion of the tibia.

5. A prosthesis as claimed in claim 4, wherein the thicker cylindrical section and the narrower cylindrical section (14, 15) of said first means are interconnected by a conical intermediate section (16).

6. A prosthesis as claimed in claim 2, wherein said first means (13) has a cavity for receiving a connection member (8) included in the mechanism and mounted to the socket.

7. A prosthesis as claimed in claim 6, wherein said cavity is located in a separate, exchangeable member (17) screwed into said first means (13).

8. A prosthesis as claimed in claim 7 wherein the connection member comprises a pin (8) having an inner end shaped like a ball (8a) detachably seated in the cavity of the exchangeable member (17).

9. A prosthesis as claimed in claim 6, wherein the mechanism includes a resilient plate (5) which comprises an elastic, high tensile strength material having an opening (7) for the passage of the connection member (8) to parts (13–17) of the mechanism adapted to be located in the tibia (T), said resilient plate exhibiting multidirectional resilience properties which yield a tunable transfer of forces between the tibia and the socket.

10. A prosthesis as claimed in claim 2, wherein portions (13, 17) of the mechanism adapted to be in direct contact with tissues of the stump (S) comprise a biocompatible material.

11. A prosthesis as claimed in claim 10, wherein said biocompatible material is pure titanium.

* * * * *